United States Patent [19]

Suga

[11] Patent Number: 4,613,235
[45] Date of Patent: Sep. 23, 1986

[54] METHOD AND APPARATUS FOR MEASURING GLOSS WHICH CORRELATES WELL WITH VISUALLY ESTIMATED GLOSS

[76] Inventor: Shigeru Suga, 20-2, Yoyogi 5-chome, Shibuya-ku, Tokyo, Japan

[21] Appl. No.: 701,193

[22] Filed: Feb. 13, 1985

[30] Foreign Application Priority Data

Feb. 29, 1984 [JP] Japan ................................ 59-38290

[51] Int. Cl.$^4$ ............................................. G01N 21/47
[52] U.S. Cl. .................................................. 356/446
[58] Field of Search ................ 356/445, 446, 447, 448

[56] References Cited

U.S. PATENT DOCUMENTS 2,604,809  7/1952  Mitchell ............................ 356/446
3,718,399  2/1973  Kalman ............................. 356/446
4,184,082  1/1980  Peoples ............................. 356/446

OTHER PUBLICATIONS

International Standard ISO 2813, "Paints and Varnishes—Measurement of Specular Gloss of Non-Metallic Paint Films at 20°, 60° and 85°", second edition, 1978.

Primary Examiner—R. A. Rosenberger
Attorney, Agent, or Firm—Wenderoth, Lind & Ponack

[57] ABSTRACT

A method and apparatus for measuring the gloss of a surface of a material by receiving light reflected from the surface and measuring the amount of light. Parallel light rays from a light source are directed against the surface the gloss of which is to be determined at an angle of incidence, and a cross-section of light rays reflected from the surface at an angle of reflection equal to the angle of incidence is received and the central region of the cross-section of the light rays is blocked out by a light intercepting plate, so that only the light received after the blocking out of the central region is used as a determination of the gloss of the surface.

4 Claims, 6 Drawing Figures

METHOD AND APPARATUS FOR MEASURING GLOSS WHICH CORRELATES WELL WITH VISUALLY ESTIMATED GLOSS

The present invention relates to a method in which regularly-reflected light from the glossy surface of a substance is received selectively to measure visual gloss or visually received gloss, which is correlated with the sensation of luster.

BACKGROUND OF THE INVENTION

Reflected light from the glossy surface of a substance comprises regularly-reflected light from a light source in the form of an image of the light source, and diffusedly reflected light which is relected in diffused form due to the specific state of the surface of the substance. Diagrams indicating the quantities of this reflected light are shown in FIGS. 1 and 2. Illuminant light 1 from a light source (not shown) is reflected from a reflecting plane 2 and turns into regularly-reflected light 3 and diffusedly-reflected light 4. The regularly-reflected light is reflected in the direction of the regular reflection angle which is equal to the incident angle $\theta$, while the diffusedly-reflected light is reflected around the regularly reflected light. FIG. 1 shows the state in which the central region of the reflected light is narrow and sharply defined and of relatively high intensity, and the intensity of the diffusedly-reflected light is relatively low since the regular reflection is strong. FIG. 2 shows the state in which the central region of the reflected light is broad and not well defined and of relatively low intensity, and the diffusedly-reflected light is large since the regular reflection is weak. Since every light source has a specific size, the illuminant light 1 is a bundle of rays having specific dimensions; consequently, the regularly-reflected light therefrom also occupies a regularly-reflected light area 3 of specific dimensions, while the diffusedly-reflected light area 4 is located around the area 3.

For describing the reflection characteristics of this glossy surface of a substance, the terms "gloss" and "glossiness" or "luster" (for a feeling of luster) are used. One prior art method of measuring the degree of the gloss is the specular gloss measuring method (JIS Z8741 Method of Measurement for Glossiness). FIG. 3 shows the structure of a specular gloss meter used in this method. Light from a light source in the form of a lamp 5 passes through a lens 6, is focussed thereby on a slit 7, and is further turned into parallel rays by a lens 8. These light rays are reflected from the surface 2 of a substance the gloss of which is to be measured, and are focussed on a receiver stop 10 by a lens 9, and then reach a photoelectric cell 12 of a receiver 11. The light received by said photoelectric cell 12 is that condensed in the stop 10 by the lens 9 in this structure. Therefore, the light passing through the stop 10 is only regularly-reflected light containing light moving parallel to an optical axis in the direction of regular reflection, or light deviating slightly therefrom, and thus diffusedly-reflected light in the vicinity of the regularly-reflected light which intersects the optical axis of the regular reflection or is divergent therefrom does not strike the aperture of the stop and thus is not received by the photoelectric cell. Consequently, the cell receives only light regularly or directly reflected from the light source. FIG. 4 shows the cross-section of the direct light received by the cell. Said cross-section is composed of the central portion 14 of the illuminant light having the same size as the image 13 of an illuminant filament, and regularly-reflected light 15 surrounding said portion. The specular gloss meter thus constructed is generally used widely for evaluating gloss of the surface of a substance.

However the specular gloss measured thereby does not correlate well with a visual estimation of gloss. At the present neither a gloss measuring method nor a gloss meter which correlates well with the result of visual measurement has been developed.

In view of the actual state of this prior art of measuring gloss, the present inventors further studied the reason why gloss measured with the conventional gloss meter, namely the specular gloss meter, does not correlate well with that estimated visually.

Generally, the intensity of regularly-reflected light obtained from the reflection of illuminant light on a specular plane is called "brightness", while the intensity of reflected light in the vicinity of the regularly-reflected light, which comprises the reflection from the surface of a substance and the internal reflection in a surface coating layer, is called the "specific luster" attributed to the surface of the substance. In the case of a smooth plane on which the brightness is high while the specific luster is low, the human eye is apt to sense the high brightness as glare, while being unable to preceive specific luster. Hence, the eye makes a comparison on the basis of the intensity of the glare. Therefore, a high degree of correlation exists between specular gloss and visual estimation in this case.

In the case of a surface of a substance which is not so smooth, the human eye tries instinctively to preceive the specific luster of the substance, keeping away glare caused by brightness. Hence, specular gloss measured by receiving brightness of direct light from a light source and regularly-reflected light around said direct light together has a poor correlation with the visual estimation of that gloss. Moreover, in the case of a surface close to a matte surface in texture, on which brightness is very low, the ratio of the specific luster of the surface of the substance to the brightness is relatively large. Hence, correlation between measured speeular gloss and visual estimation of gloss is relatively high.

For these reasons, the incident angle of the illuminant light is changed in accordance with the smoothness of the surface of the substance to be tested when measurement is conducted according to the above-described specular gloss measuring method. In the method of JISZ8741, it is provided that the measurement is to be conducted with the incident angle set at 20 degrees when specular gloss is comparatively high, at 45 or 60 degrees when it is intermediate, and at 75 to 85 degrees when it is low. Even though measurement is conducted for 20 degree gloss, 60 degree gloss or other angle gloss by varying the incident angle in this way, gloss values obtained by this measurement do not correlate well with visual estimation of gloss.

Based on the results of the above-described studies, the present inventors concluded that specular gloss did not correlate well with visual estimation of gloss in the prior art because said gloss is regarded thereby as involving the central region of the regularly-reflected light, and thus the discrepency between specular gloss and visually estimated gloss cannot be eliminated even with the cumbersome method in which 20 degree gloss, 60 degree gloss and other gloss must be measured separately. The present inventors have confirmed that a gloss measuring method eliminating said disadvantage of the prior art can be provided according to the present invention.

SUMMARY OF THE INVENTION

The present invention provides a method and apparatus for measuring gloss which correlates well with visually estimated gloss, which invention intercepts a bundle of directly and regularly-reflected rays of illuminant light, the central region 14 of the illuminant light in FIG. 4, and causes regularly-reflected light around said bundle of rays, denoted by numeral 15 in FIG. 4 to be received by a photoelectric cell so that "visual gloss" as the gloss measured by the method of the present invention will be called hereinafter, which has a strong correlation with visually estimated gloss can be measured for the glossy surfaces of all substances irrespective of the intensity of gloss.

DETAILED DESCRIPTION OF A PREFERRED EMBODIMENT

A preferred embodiment of the present invention will be described with reference to FIG. 5.

Figure 1:
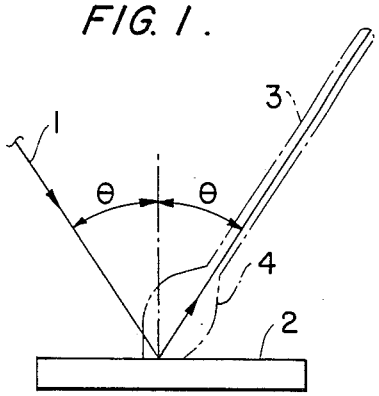
FIGS. 1 and 2 are diagrams of the quantities of light reflected from a plane surface.
Figure 2:
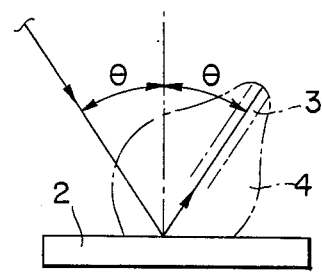
Figure 3:
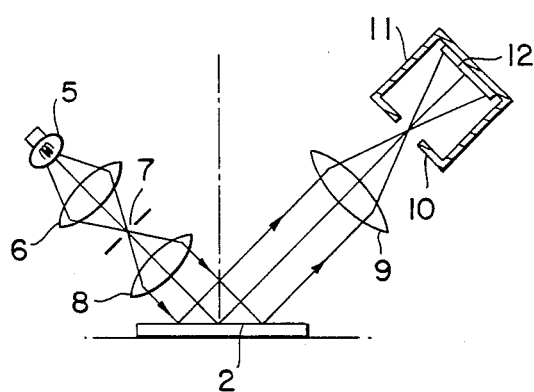
FIG. 3 is a diagram of a conventional specular gloss measuring method.
Figure 4:
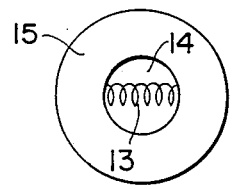
FIG. 4 is a cross-section of a bundle of regularly-reflected rays at a slit in the diagram of FIG. 3.
Figure 5A:
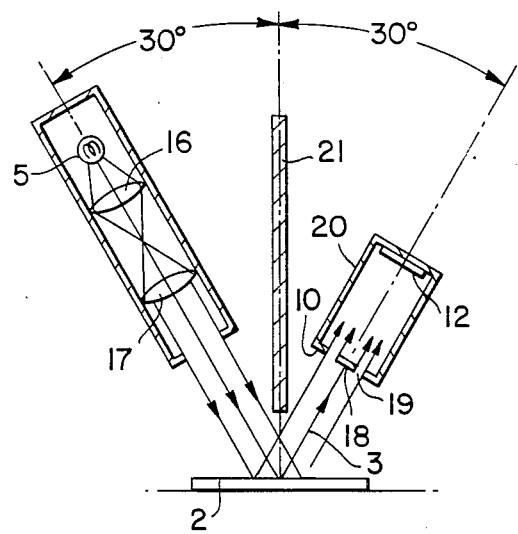
FIG. 5a is a diagrammatic section of an apparatus for measuring visual gloss according to the present invention.
Figure 5B:
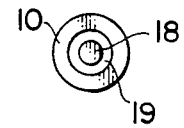
FIG. 5b is an end view of the light receiver.

In FIGS. 5a and 5b, light from a light source in the form of a lamp 5 is turned into parallel light rays by two lenses 16 and 17 and these rays are reflected from the reflecting surface 2 of the substance the gloss of which is to be measured. The central region (denoted by numeral 14 in FIG. 4) of the bundle of regularly-reflected rays is intercepted by a circular light-intercepting plate 18 positioned in the center of a stop, and only the peripheral region of the bundle of the regularly-reflected rays (denoted by numeral 15 in FIG. 4) enters a light receiver 20 through a ring-shaped opening 19 and is received by a photoelectric cell 12. In the present embodiment, the incident angle and the reflection angle are set to be 30 degrees, and a partition plate 21 is provided on the boundary between the light source side and the light receiver side. Also, the diameter of the photoelectric cell 12 is made larger than the diameter of the outer circumference of the ring-shaped opening.

The essence of the present invention lies in the condition that the central region of the regularly-reflected illuminant light is intercepted and only the regularly-reflected light around said region is received. With this new method, which has not been thought of heretofore, it has become possible to attain an unparalleled effect, namely, to obtain a measured value of gloss which correlates with the visually estimated gloss irrespective of the intensity of gloss.

The construction of the above-described embodiment of the present invention achieves results as set forth in the following.

(1) The conditions of light reception correlate optically with those in which the human eye perceives light, since the light is not concentrated by a lens on the reflection side of the system.

(2) The glaring regularly directly-reflected light from the light source in the central region of the regularly-reflected light is not received.

(3) The incident and reflection angles of 30 degrees are substantially intermediate between those for objects of high and intermediate gloss measured by the convention gloss meter, and are able to cover the gloss of such objects. With respect to an object of low gloss, reflected light therefrom is caught effectively by the broad ring-shaped opening.

(4) The partition plate 21 removes the effects of scattered light reflected from a substance the gloss of which is to be measured and stray light from the light source.

The effect of the present invention will now be explained by way of comparison between visual gloss (called so because of its excellent correlation with visually estimated gloss) obtained by the gloss measuring method and apparatus of the present invention and specular gloss obtained by the conventional method.

Table 1 was prepared by ranking gloss determined by visual estimation, specular gloss (two examples with the incident and reflection angles set at 20 and 60 degrees respectively) measured according to the conventional method and with the conventional apparatus and visual gloss measured according to the present invention, for the same ten coated sample plates, and comparing the values and rankings with one another. The values of specular gloss were obtained according to the conventional method and apparatus, that is the method and apparatus of JISZ8741, and those of visual gloss were obtained according to the present invention by using the same reference surface and the same conditions, e.g. light intensity as in JISZ8741. As for specular gloss according to the conventional method, the 60° gloss values for five samples are different from the results obtained by visual determination, and the difference is particularly large in sample No. 1. Moreover, the measured values for samples Nos. 2, 3, 4, 5, 6 and 10 are nearer to the results of visually determined gloss and gloss determined according to the present invention. Although measurement is generally conducted with respect to 60° gloss, the performance of this measurement in discriminating the feeling of gloss or luster is very low. As to the 20° gloss, the values of samples Nos. 1 and 6 measured by the conventional method and apparatus are different from the results obtained by visual determination and by the present invention, and the difference for sample No. 6 is large. Conversely, the values of visual gloss according to the present invention correlate well with the results obtained by visual determination.

TABLE 1

| Sample No. | Ranking gloss according to visual determination | Specular gloss according to conventional method | | | | Visual gloss value according to the present invention | |
|---|---|---|---|---|---|---|---|
| | | 20° gloss value | | 60° gloss value | | | |
| | | % | Ranking | % | ranking | % | ranking |
| 1 | Δ | 28.7 | X | 71.0 | XX | 40.1 | Δ |
| 2 | Δ | 35.8 | Δ | 80.0 | Δ | 43.4 | Δ |

TABLE 1-continued

| Sample No. | Ranking gloss according to visual determination | Specular gloss according to conventional method | | | | Visual gloss value according to the present invention | |
|---|---|---|---|---|---|---|---|
| | | 20° gloss value | | 60° gloss value | | | |
| | | % | Ranking | % | ranking | % | ranking |
| 3 | Δ | 36.0 | Δ | 82.5 | Δ | 40.8 | Δ |
| 4 | X | 27.9 | X | 80.7 | Δ | 39.8 | X |
| 5 | ⊚ | 69.5 | ⊚ | 89.8 | ○ | 53.1 | ⊚ |
| 6 | ○ | 34.2 | X | 82.3 | Δ | 46.1 | ○ |
| 7 | ⊚ | 70.9 | ⊚ | 91.4 | ⊚ | 52.7 | ⊚ |
| 8 | XX | 7.7 | XX | 42.8 | XX | 17.6 | XX |
| 9 | XX | 16.2 | XX | 60.4 | XX | 31.9 | XX |
| 10 | Δ | 43.6 | Δ | 86.7 | | 42.8 | Δ |
| Classification of ranking | best ⊚ | 65 and above | ⊚ | 90 and above | ⊚ | 50 and above | ⊚ |
| | good ○ | 50~64.9 | ○ | 85~89.9 | ○ | 45~49.9 | ○ |
| | ordinary Δ | 35~49.9 | Δ | 80~84.9 | Δ | 40~44.9 | Δ |
| | bad X | 20~34.9 | 82 X | 75~79.9 | X | 35~39.9 | X |
| | worst XX | 19 and below | XX | 74 and below | XX | 34 and below | XX |

What is claimed is:

1. In a method of measuring the gloss of a surface of a material by receiving light reflected from the surface and measuring the amount of light, the improvement comprising directing parallel light rays from a light source against the surface the gloss of which is to be determined at an angle of incidence, receiving a cross-section of light rays reflected from the surface at an angle of reflection equal to the angle of incidence, blocking out the central region of the cross-section of the light rays received, and measuring only the light received after the blocking out of the central region and using the measured amount as a determination of the gloss of the surface.

2. An apparatus for measuring visual gloss, comprising:
light source means for directing parallel light rays against a surface the gloss of which is to be detected at an angle of incidence;
light receiver means positioned for receiving light rays reflected at an angle of reflection equal to the angle of incidence from the surface, said light receiver means having a light admitting opening of a predetermined shape and receiving and measing means for receiving the light from said admitting opening and a light intercepting plate between the surface and said light receiving and measuring means and having a shape for intercepting and blocking light in the central area of said admitting opening from reaching said light receiving and measuring means.

3. An apparatus as claimed in claim 2 in which said opening is circular and said light intercepting plate is circular and is in the middle of said opening.

4. An apparatus as claimed in claim 2 further comprising a further light intercepting plate between said light source means and said light receiver means and spaced above the surface for blocking stray light from said light source means from reaching said light receiver means.

* * * * *